(12) United States Patent
Kang et al.

(10) Patent No.: US 10,285,641 B2
(45) Date of Patent: May 14, 2019

(54) VITAL SIGNAL MEASURING WATCH AND METHOD FOR MEASURING VITAL SIGNAL

(71) Applicant: Kyungpook National University Industry-Academic Cooperation Foundation, Buk-Gu, Daegu (KR)

(72) Inventors: Soon Ju Kang, Daegu (KR); Cheol Soo Ahn, Daegu (KR); Kyung Chun Lee, Incheon (KR); Yu Jin Park, Gumi-si (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 901 days.

(21) Appl. No.: 14/780,237

(22) PCT Filed: Mar. 26, 2014

(86) PCT No.: PCT/KR2014/002559
§ 371 (c)(1),
(2) Date: Sep. 25, 2015

(87) PCT Pub. No.: WO2014/157945
PCT Pub. Date: Oct. 2, 2014

(65) Prior Publication Data
US 2016/0051192 A1    Feb. 25, 2016

(30) Foreign Application Priority Data

Mar. 26, 2013 (KR) .................. 10-2013-0032253

(51) Int. Cl.
*A61B 5/00* (2006.01)
*A61B 5/0205* (2006.01)
*A61B 5/021* (2006.01)

(52) U.S. Cl.
CPC .............. *A61B 5/681* (2013.01); *A61B 5/002* (2013.01); *A61B 5/0022* (2013.01); *A61B 5/021* (2013.01);
(Continued)

(58) Field of Classification Search
CPC ..... A61B 5/002; A61B 5/0205; A61B 5/0022; A61B 5/021
See application file for complete search history.

(56) References Cited

U.S. PATENT DOCUMENTS 8,945,017 B2 *   2/2015   Venkatraman ......... A61B 5/721
                                                   600/500
2011/0021930 A1  1/2011   Mazzeo et al.
2011/0054282 A1* 3/2011   Nekoomaram ...... A61B 5/0002
                                                   600/347

FOREIGN PATENT DOCUMENTS

JP    H09238908 A    9/1997
JP    H11289394 A   10/1999
(Continued)

OTHER PUBLICATIONS

International Preliminary Report on Patentability dated Oct. 8, 2015 issued in corresponding International Application No. PCT/KR2014/002559 (with English translation).
(Continued)

*Primary Examiner* — Christian Jang
(74) *Attorney, Agent, or Firm* — Harness, Dickey & Pierce, P.L.C.

(57) ABSTRACT

A vital signal measuring watch is provided, the vital signal measuring watch including a watch module having a shape of a wrist watch, wherein the watch module includes a device receiving portion at one side of the watch module and a communication port in the device receiving portion; and a vital signal sensor connected to or disconnected from the device receiving portion, connected to the communication
(Continued)

port when being connected to the device receiving portion, and configured to transmit biometric data obtained by measuring vital signals to the communication port, wherein the vital signal sensor is configured to generate an interrupt plug-in event to transmit the event to the watch module when being connected to the communication port, and the watch module is configured to count a number of interrupts of the transmitted interrupt plug-in event, automatically recognize a communication protocol supported by the vital signal sensor according to the number of interrupts, and dynamically activate a communication interface to correspond to the recognized communication protocol to receive the biometric data from the vital signal sensor.

20 Claims, 12 Drawing Sheets

(52) U.S. Cl.
CPC .............. *A61B 5/0205* (2013.01); *A61B 5/72* (2013.01); *A61B 5/742* (2013.01); *A61B 2560/0475* (2013.01); *A61B 2562/08* (2013.01)

(56) References Cited

FOREIGN PATENT DOCUMENTS

| | | |
|---|---|---|
| JP | 2007-025120 A | 2/2007 |
| JP | 2011-519588 A | 7/2011 |
| KR | 10-0319948 B1 | 1/2002 |
| KR | 10-2005-008421 A | 1/2005 |
| KR | 10-2005-0050350 A | 5/2005 |
| KR | 10-2006-0036497 A | 5/2006 |
| KR | 10-2009-0107414 A | 10/2009 |
| KR | 10-2010-0139024 A | 12/2010 |
| KR | 10-2012-0119154 A | 10/2012 |
| WO | WO-2009/127954 A2 | 10/2009 |
| WO | WO-2012/092303 A1 | 7/2012 |

OTHER PUBLICATIONS

International Search Report PCT/ISA/210 for International Application No. PCT/KR2014/002559 dated May 27, 2014.

* cited by examiner

VITAL SIGNAL MEASURING WATCH AND METHOD FOR MEASURING VITAL SIGNAL

CROSS-REFERENCE TO RELATED APPLICATIONS

This application is a national phase under 35 U.S.C. § 371 of PCT International Application No. PCT/KR2014/002559 which has an International filing date of Mar. 26, 2014, which claims priority to KR 10-2013-0032253 filed Mar. 26, 2013; the entire contents of each of which are hereby incorporated by reference.

TECHNICAL FIELD

The present disclosure relates to a vital signal measuring watch and a method for measuring a vital signal. The present disclosure is derived from a study conducted as one of software computing industry source technology development project supported by Ministry of Knowledge Economy, Republic of Korea (No. 201227650100, and Title: Development of Self-organizing Software platform (SoSp) for welfare devices).

BACKGROUND ART

In recent, with the advent of ubiquitous age in which people may connect to a network environment anytime and anywhere through the development of technology, the scale and range of an information technology connected to a network have also been expanded to keep pace with it, and with the advent of aging society and the growth of the industry aimed for the aged, many people pay attention to health and medical fields, so it is possible to use various medical services, such as remote diagnosis or disease management without visiting a hospital by using an ubiquitous technology for healthcare. For example, a patient suffering from diabetes may use a blood sugar meter to check his or her blood sugar for himself or for herself without visiting a hospital.

However, according to a typical technology, there is inconvenience that the patient suffering from diabetes should regularly check blood sugar and separately write measured records through handwriting. Thus, there is a need for a vital signal measuring device that may easily measure a vital signal, such as blood sugar, monitor the state of a patient anytime and anywhere even while the patient is out, and rapidly cope with emergency.

DISCLOSURE OF THE INVENTION

Technical Problem

Embodiments provide a vital signal measuring watch and a method for measuring a vital signal that may perform biometrics only with an easy and simple operation.

Embodiments also provide the convenience of vital signal measurement by enabling the multiple devices of various vital signal sensors to be linked to a single watch module.

Embodiments also provide an effective medial service by easily collecting personal data on a user and increasing the usage of data, by transmitting, biometric record data (a watch's ID, a vital signal sensor's ID, biometric data, and a measurement time) provided as a single data packet through integration, to a personal mobile terminal or an external device, such as a hospital terminal by using the wireless transmission and reception function of a watch module.

Tasks to be solved by the present disclosure are not limited to the above-mentioned tasks. Other tasks not mentioned could be clearly understood to a person skilled in the art to which the present disclosure pertains, from the following description.

Technical Solution

In one embodiment, a vital signal measuring watch includes a watch module having a shape of a wrist watch, wherein the watch module includes a device receiving portion at one side of the watch module and a communication port in the device receiving portion; and a vital signal sensor connected to or disconnected from the device receiving portion, connected to the communication port when being connected to the device receiving portion, and configured to transmit biometric data obtained by measuring vital signals to the communication port, wherein the vital signal sensor is configured to generate an interrupt plug-in event to transmit the event to the watch module when being connected to the communication port, and the watch module is configured to count a number of interrupts of the transmitted interrupt plug-in event, automatically recognize a communication protocol supported by the vital signal sensor according to the number of interrupts, and dynamically activate a communication interface to correspond to the recognized communication protocol to receive the biometric data from the vital signal sensor.

The vital signal sensor may be configured to sense a change in power when being connected to the communication port, to generate the interrupt plug-in event.

The communication interface may be provided to support different communication protocols, and a processor of the watch module may be configured to activate at least one of the different communication protocols to correspond to the communication protocol supported by the vital signal sensor to dynamically activate the communication interface.

The communication protocol may include at least one of universal asynchronous receiver/transmitter (UART), universal serial bus (USB), serial peripheral interface (SPI), inter-integrated circuit bus ($I^2C$), programmed input/output (PIO), and analog-to-digital converter (ADC).

The watch module may include a housing having the device receiving portion at one side thereof; the communication port installed in the device receiving portion; an interrupt handler installed in the housing and configured to count the number of counts of the interrupt plug-in event; a processor installed in the housing and configured to automatically recognize the communication protocol supported by the vital signal sensor according to the number of interrupts; the communication interface installed in the housing, configured to be dynamically activated to correspond to the communication protocol by the processor, and configured to perform communication with the vital signal sensor according to the communication protocol to receive the biometric data from the vital signal sensor; a time measuring module installed in the housing and configured to measure time information; and a display unit installed at an external side of the housing and configured to display at least one of the time information and the biometric data.

The watch module may further include a memory unit, and the processor may be configured to integrate biometric record data to be a single data packet to store the single data packet in the memory unit, the biometric record data including an ID of the watch module, an ID of the vital signal sensor, the biometric data and measurement time information on the biometric data.

The watch module may further include a communication unit that is configured to transmit, to an external device, the biometric record data provided as the single data packet through integration.

The watch module may further include a state control unit configured to activate or inactivate a wireless communication function of the communication unit in a preset period, and the processor may be configured to broadcast an advertising message in a state in which the wireless communication function is activated, and set a wireless network in response to an advertising message reception signal from the external device corresponding to the advertising message.

The housing may include a communication module connection port, and the watch module further may include a communication module connected to the communication module connection port to support wireless communication with an external device.

The watch module may further include a connection port installed at the device receiving portion to be connected to the communication port, and an extension port including a plurality of device connection ports connected to a plurality of vital signal sensors that measures different vital signals.

The processor may be configured to recognize one or more communication protocols corresponding to each of vital signal sensors, and the communication interface may be configured to receive the biometric data from each of the vital signal sensors according to a communication protocol corresponding to each of the vital signal sensors.

The watch module may further include a delay setting unit configured to set a delay to prevent collision of a plurality of interrupt plug-in events from the plurality of vital signal sensors to sequentially process the plurality of interrupt plug-in events.

The processor may be configured to transmit an ID request message for checking a function of the vital signal sensor to the vital signal sensor by using an activated communication interface and activate a task corresponding to an ID of the vital signal sensor received from the vital signal sensor in response to the ID request message.

The vital signal may include at least one of blood sugar information, blood pressure information, oxygen saturation information, and pulse wave information.

In another embodiment, a vital signal measuring watch includes a watch module having a shape of a wrist watch and a device receiving portion at one side thereof, wherein the watch module is configured to count a number of interrupts of the interrupt plug-in event transmitted from a vital signal sensor when the vital signal sensor is connected to the device receiving portion, automatically recognize a communication protocol supported by the vital signal sensor according to the number of interrupts, and dynamically activate a communication interface to correspond to the recognized communication protocol to receive biometric data from the vital signal sensor.

In further another embodiment, a method for measuring a vital signal includes counting, by a watch module, a number of interrupts of an interrupt plug-in event transmitted from a vital signal sensor when the vital signal sensor is connected to the watch module, automatically recognizing a communication protocol supported by the vital signal sensor according to the number of interrupts, and dynamically activating a communication interface to correspond to the communication protocol; and receiving, by the watch module, biometric data from the vital signal sensor by using the activated communication interface.

The method may further include integrating and storing, by the watch module, biometric record data to be a single data packet, the biometric record data including an ID of the watch module, an ID of the vital signal sensor, the biometric data and measurement time information on the biometric data; and transmitting, by the watch module, the biometric record data provided as the single data packet through integration, to an external device.

The transmitting of the biometric record data to the external device may include activating or inactivating, by the watch module, a wireless communication function in a preset period; broadcasting, by the watch module, an advertising message in a state in which the wireless communication function is activated; and setting, by the watch module, a wireless network in response to an advertising message reception signal from the external device corresponding to the advertising message.

The activating of the communication interface may include setting a delay to sequentially process the plurality of interrupt plug-in events to prevent collision of a plurality of interrupt plug-in events from a plurality of vital signal sensors.

The method may further include, between the activating of the communication interface and the receiving of the biometric data, transmitting, by the watch module, an ID request message for checking a function of the vital signal sensor to the vital signal sensor by using the activated communication interface; and activating, by the watch module, a task corresponding to an ID of the vital signal sensor received from the vital signal sensor in response to the ID request message.

Advantageous Effects

According to an embodiment of the present disclosure, since it is possible to perform biometrics only with an easy and simple operation, even a user who is unfamiliar with the usage of an electronic device may easily perform biometrics.

An embodiment of the present disclosure also provides the convenience of vital signal measurement by enabling the multiple devices of various vital signal sensors (a blood sugar meter, a sphygmomanometer, an oxygen saturation meter, a pulse meter, etc.) to be linked to a single watch module.

An embodiment of the present disclosure may also provide an effective medial service by easily collecting personal data on a user and increasing the usage of data, by transmitting, biometric record data (a watch's ID, a vital signal sensor's ID, biometric data, and a measurement time) provided as a single data packet through integration, to a personal mobile terminal or an external device, such as a hospital terminal by using the wireless transmission and reception function of a watch module.

The effects of the present disclosure are not limited the above-described effects. Effects not mentioned could be clearly understood to a person skilled in the art to which the present disclosure pertains, from the description and the accompanying drawings.

MODE FOR CARRYING OUT THE INVENTION

Figure 1:
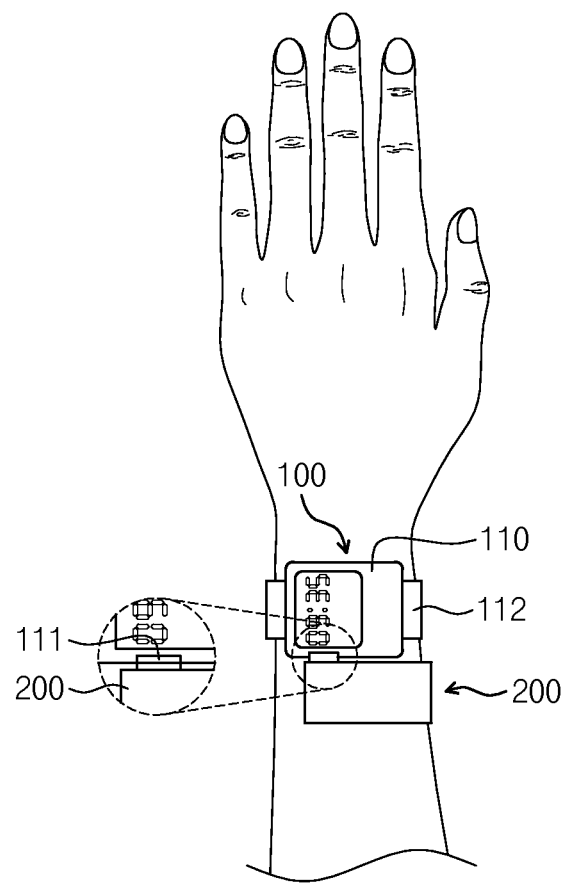
FIG. 1 is a diagram showing the usage state of a vital signal measuring watch according to an embodiment of the present disclosure.

Other advantages and features of the present disclosure, and implementation methods thereof will be clarified through following embodiments to be described in detail with reference to the accompanying drawings. The present disclosure may, however, be embodied in different forms and should not be construed as limited to the embodiments set forth herein. Rather, these embodiments are provided so that this disclosure is thorough and complete and fully conveys the scope of the present disclosure to a person skilled in the art to which the present disclosure pertains. Further, the present disclosure is only defined by scopes of claims.

Although some terms are not defined, all the terms used herein (including technology or science terms) have the same meanings as those generally accepted by typical technologies in the related art to which the present invention pertains. The terms defined in general dictionaries may be construed as having the same meanings as those used in the related art and/or a text of the present application and even when some terms are not clearly defined, they should not be construed as being conceptual or excessively formal.

The term "unit" used herein may mean a unit for processing at least one function or operation. For example, it may mean a hardware component such as an FPGA or an ASIC. However, the term "unit" is not limited to the software or the hardware. The term "unit" may be configured in an addressable storage medium or may be configured to operate one or more processors. Thus, as an example, the "unit" includes components such as software components, object-oriented software components, class components, and task components; processes, functions, attributes, procedures, sub routines, program code segments, drivers, firmware, micro codes, circuits, data, DBs, data structures, tables, arrays and variables. A function provided in the "unit" may be divided into sub components or may be provided through integration with another "unit".

The meaning of a 'connection' of a component to another component in the description includes a direct connection through the third component as well as a direct connection between two components. General descriptions of known configurations may be left out in order not to obscure the subject matter of the present disclosure.

A vital signal measuring watch according to an embodiment of the present disclosure includes a watch module that may be connected to or disconnected from a vital signal sensor (e.g., a blood sugar meter or sphygmomanometer). The watch module is a host module provided to have the shape of a wrist-watch, automatically checks the communication protocol and function of the vital signal sensor when being connected to one or more vital signal sensors, dynamically activates a communication interface suitable for a corresponding vital signal sensor, and activates a task according to the function of the corresponding vital signal sensor to operate the vital signal sensor and collect corresponding biometric data from the vital signal sensor.

For the vital signal measuring watch according to an embodiment of the present disclosure, when the vital signal sensor is connected to the watch module, the vital signal sensor generates an interrupt plug-in event corresponding to the communication protocol of the vital signal sensor to transmit the generated event to the watch module, and the watch module counts the number of interrupts of the interrupt plug-in event from the vital signal sensor, automatically recognize a communication protocol supported by the vital signal sensor according to the number of interrupts and dynamically activates a communication interface to correspond to the communication protocol of the vital signal sensor.

Thus, since only with the plug-in operation of the vital signal sensor and the watch module by a user, the watch module automatically sets a communication method with the vital signal sensor, and activates a task suitable for the function of the vital signal sensor, it is easy to use and it is suitable for a user to collect various vital signals for himself or for herself by using various vital signal sensors.

The vital signal measuring watch according to the embodiment of the present disclosure integrates biometric data measured through the vital signal sensor, a watch module's ID, a vital signal sensor's ID, and measurement time information on the biometric data to form a biometric record material as a single data packet. Since the watch module's ID one to one corresponds to a user ID, it may be said that the watch module's ID represents the user ID. The biometric record material as the single data packet provided through integration may be transmitted to a user's person mobile terminal or an external device, such as a hospital server and it is possible to altogether check biometric data on a user through a corresponding external device.

FIG. 1 is a diagram showing the usage state of a vital signal measuring watch according to an embodiment of the present disclosure. Referring to FIG. 1, a vital signal measuring watch 10 according to an embodiment of the present disclosure includes a watch module 100 and a vital signal sensor 200. The watch module 100 is provided with the similar shape to a general wrist watch. In the embodiment shown in FIG. 1, the vital signal sensor 200 is a blood sugar meter that measures the blood sugar of a human body. However, it is an example and the vital signal sensor 200 may be a sensor that measures other vital signals, e.g., blood pressure, oxygen saturation or a pulse wave.

Figure 2:
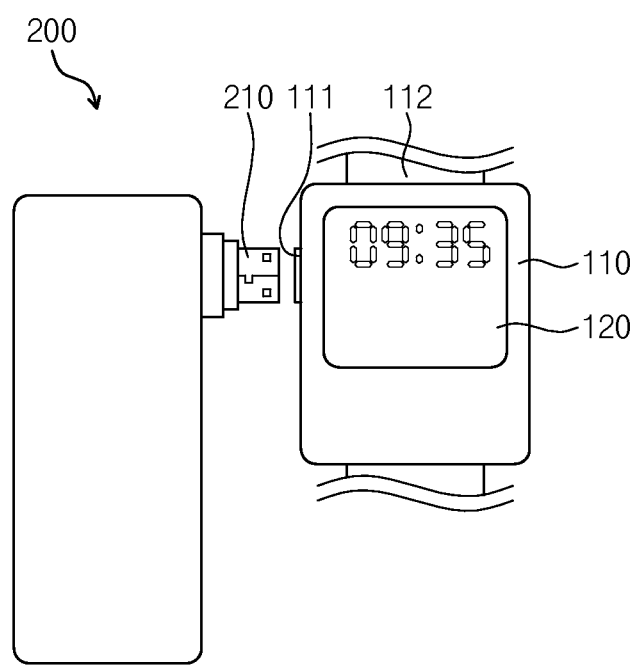
FIG. 2 is a diagram showing a watch module and a vital signal sensor that configure a vital signal measuring watch according to an embodiment of the present disclosure.

FIG. 2 is a diagram showing a watch module and a vital signal sensor that configure a vital signal measuring watch according to an embodiment of the present disclosure.

Referring to FIGS. 1 and 2, the watch module 100 includes a housing 110 to both sides of which a watch strap 112 is connected, and a display unit 120 on the front of the housing 110, like a general wrist watch. The watch module 100 represents the current time through the display unit 120 as the original operation of the general wrist watch in a state in which the vital signal sensor 200 is not connected to the watch module.

The vital signal sensor 200 measures vital signals to generate biometric data and has a connector 210 on its one side to transmit the biometric data to the watch module 100. The connector 210 of the vital signal sensor 200 is formed with a shape corresponding to a device receiving portion 111 that is provided on one side of the housing 110 of the watch module 100, and is provided to be capable of being inserted into or separated from the device receiving portion 111.

A communication port 130 (see FIG. 3) is disposed in the device receiving portion 111, and when the vital signal sensor 200 is engaged with the housing 110, the connector 210 is connected to the communication port 130 within the device receiving portion 111. The vital signal sensor 200 senses a connection of the communication port 130 and the connector 210 when being connected to the watch module 100, and generates a corresponding interrupt plug-in event to transmit the generated event to the watch module 100.

The watch module 100 counts the number of interrupts of the interrupt plug-in event from the vital signal sensor 200 and automatically recognizes a communication protocol supported by the vital signal sensor 200 according to the number of interrupts. The watch module 100 may dynamically activate a communication interface 160 (see FIG. 3) to correspond to the recognized communication protocol and receive biometric data from the vital signal sensor 200.

Figure 3:
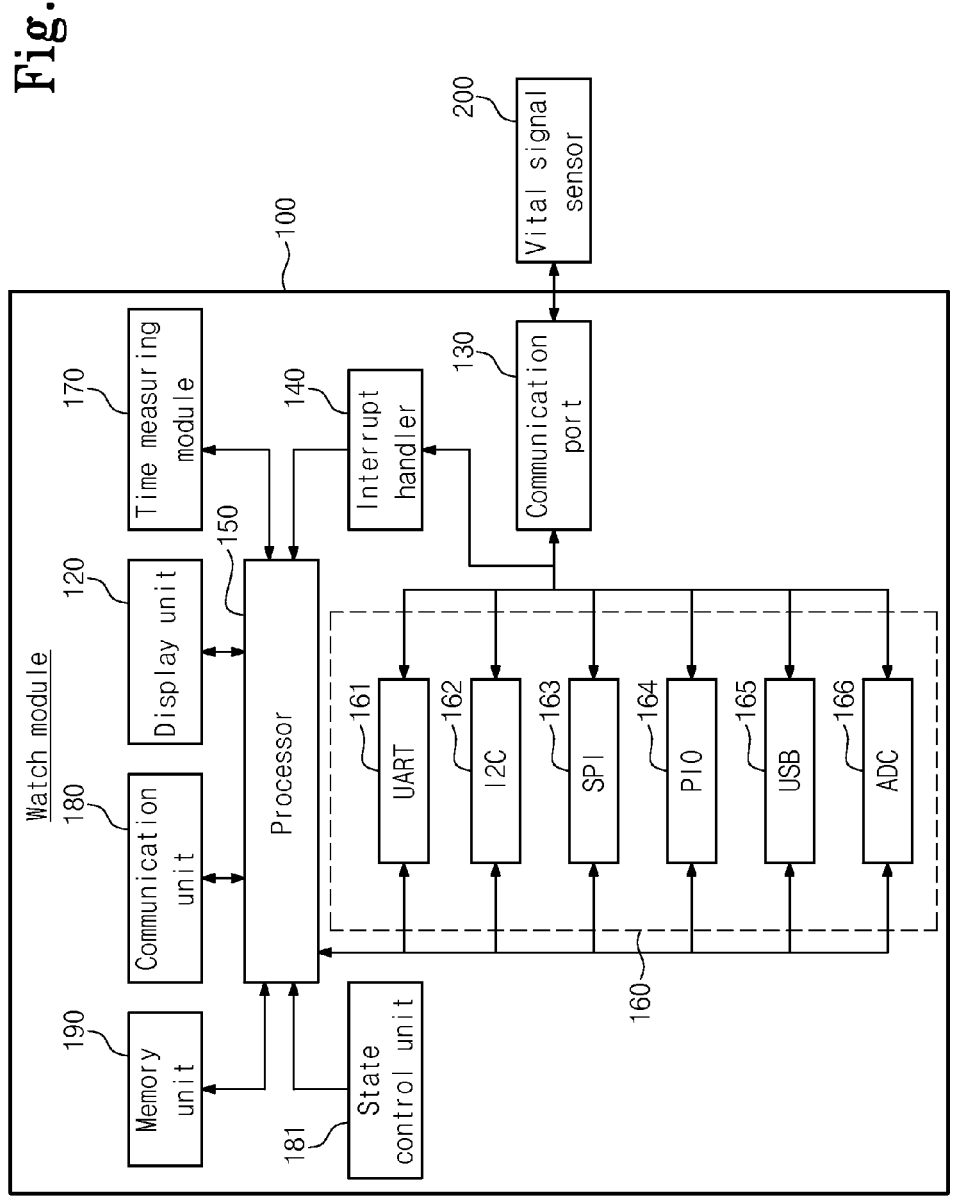
FIG. 3 is a block diagram of a vital signal measuring watch according to an embodiment of the present disclosure.

FIG. 3 is a block diagram of a vital signal measuring watch according to an embodiment of the present disclosure. Referring to FIGS. 1 to 3, the watch module 100 includes the housing 110, the display unit 120, the communication port 130, an interrupt handler 140, a processor 150, the communication interface 160, a time measuring module 170, a communication unit 180, a state control unit 181, and a memory unit 190. The display unit 120, the communication port 130, an interrupt handler 140, a processor 150, the communication interface 160, the time measuring module 170, the communication unit 180, the state control unit 181, and the memory unit 190 may be disposed in the housing 110.

The communication port 130 is connected to the connector 210 of the vital signal sensor 200 when the watch module 100 and the vital signal sensor 200 are connected, and performs communication between the watch module 100 and the vital signal sensor 200 according to the communication protocol that is set according to the communication interface 160 activated by the processor 150. As in an embodiment shown in FIGS. 8 and 10 to be described below, when a plurality of vital signal sensors 200a and 200b are connected to the watch module 100 by using an extension port 400, the communication port 130 is connected to the connection port 410 (see FIG. 9) of the extension port 400 but even in this case, it may be said that the communication port 130 is electrically connected to the connector 210 of each of the vital signal sensors 200a and 200b.

Figure 4:
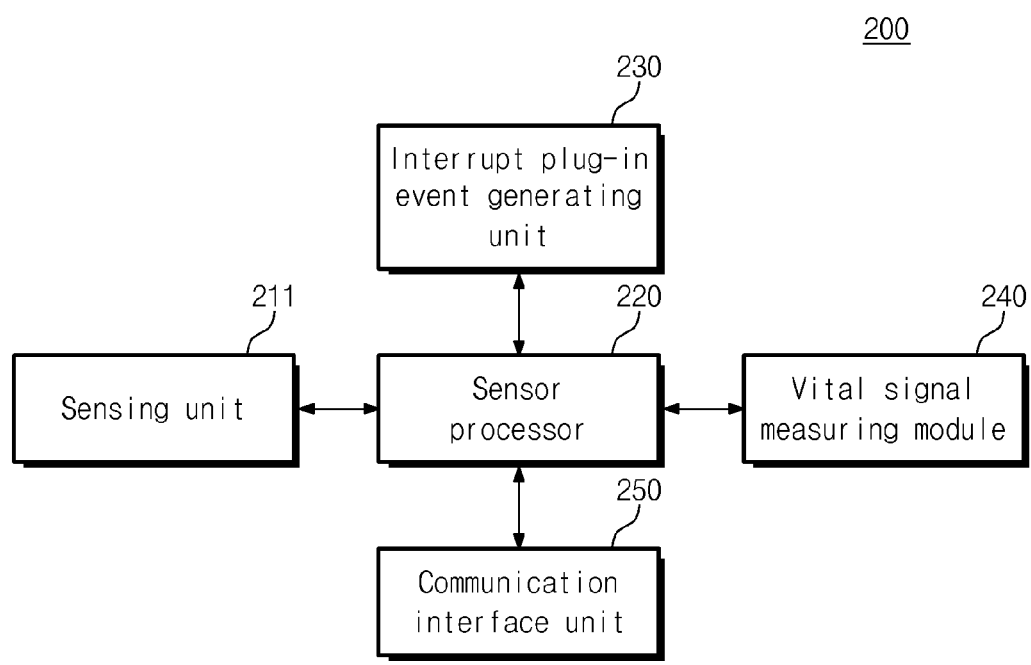
FIG. 4 is a block diagram of a vital signal sensor that configures a vital signal measuring watch according to an embodiment of the present disclosure.

FIG. 4 is a block diagram of a vital signal sensor that configures a vital signal measuring watch according to an embodiment of the present disclosure. Referring to FIGS. 1 to 4, the vital signal sensor 200 includes a sensing unit 211, a sensor processor 220, an interrupt plug-in event generating unit 230, a vital signal measuring module 240, and a communication interface unit 250.

The sensing unit 211 senses a change in power when the connector 210 of the vital signal sensor 200 is inserted into the device receiving portion 111 of the watch module 100 to be connected to the communication port, and inputs a sensing signal to the sensor processor 220 when the change in power is sensed. The sensor processor 220 recognizes a connection between the connector 210 and the communication port 130 according to the sensing signal from the sensing unit 211 to generate a control signal.

According to the control signal of the sensor processor 220, the interrupt plug-in event generating unit 230 generates an interrupt plug-in event. In this case, the interrupt plug-in event generating unit 230 generates the interrupt plug-in event as many as the number of interrupts corresponding to the communication protocol of the communication interface 250 set for each vital signal sensor 200.

The vital signal measuring module 240 measures vital signals to generate biometric data. The vital signal measuring module 240 may measure vital signals, e.g., blood pressure, oxygen saturation or a pulse wave. The communication interface unit 250 would perform communication with the watch module 100 according to a pre-defined communication protocol.

Referring back to FIGS. 1 to 3, the interrupt handler 140 counts the number of interrupts of the interrupt plug-in event from the vital signal sensor 200. The information on the number of interrupts calculated by the interrupt handler 140 is input to the processor 150 in order to check the communication protocol and function of the vital signal sensor 200.

The processor 150 automatically recognizes the communication protocol supported by the vital signal sensor 200 according to the number of interrupts. The processor 150 dynamically activates the communication interface 160 to correspond to the recognized communication protocol. That is, the processor 150 may dynamically sets the communication protocol of the communication interface 160 corresponding to a communication protocol that is differently provided for each vital signal sensor 200.

The communication interface 160 is dynamically activated to correspond to the communication protocol of the vital signal sensor 200 by the processor 150, and performs communication with the vital signal sensor 200 according to the communication protocol activated to receive biometric data from the vital signal sensor 200. The communication interface 160 may be provided to support different communication protocols.

In an embodiment, the communication interface 160 may support a universal asynchronous receiver/transmitter (UART) communication protocol 161, a inter-integrated circuit bus (I²C) communication protocol 162, a serial peripheral interface (SPI) communication protocol 163, a programmed input/output (PIO) communication protocol 164, a universal serial bus (USB) communication protocol 165, and an analog-to-digital converter (ADC) communication protocol 166.

The processor 150 automatically recognizes a communication protocol corresponding to the communication protocol supported by the vital signal sensor 200 among different communication protocols 161 to 166 supported by the communication interface 160, according to the number of interrupts calculated by the interrupt handler 140. Thus, by dynamically activating the communication interface 160 of the watch module 100 corresponding to various vital signal sensors 200, it is possible to set a communication network between the watch module 100 and the vital signal sensor 200 automatically and in real time simultaneously with the connection of the vital signal sensor 200.

The communication port 130 may perform communication with the vital signal sensor 200 according to one or more of the communications protocols of the communication interface 160 activated by the processor 150 to receive biometric data from the vital signal sensor 200. The watch module 100 may communicate with the vital signal sensor 200 through a serial bus, e.g., UART, USB, SPI, I²C, PIO, or ADC provided by the communication interface 160.

In order to check the function of the vital signal sensor 200, the processor 150 uses the activated communication interface 160 to transmit an ID request message for requesting the ID of the vital signal sensor 200 to the vital signal sensor 200. The vital signal sensor 200 transmits the ID of the vital signal sensor 200 to the processor 150 in response to the ID request message from the watch module 100. The processor 150 activates a corresponding task according to the ID of the vital signal sensor 200.

Thus, the watch module 100 may generate a task to perform a required function according to the vital signal sensor 200 corresponding to various vital signal sensors 200 to be capable of collecting biometric data corresponding to various vital signal sensor 200.

The time measuring module 170 measures time information. The display unit 120 may display the current time measured by the time measuring module 170 or biometric data received from the vital signal sensor 200. The memory unit 190 integrates biometric record data including the ID of the watch module 100, the ID of the vital signal sensor 200, biometric data, and measurement time information on the biometric data to be a single data packet structure and stores the single data packet.

The memory unit 190 may be a volatile memory, such as a static RAM (SRAM), a dynamic RAM (DRAM), a synchronous DRAM (SDRAM), etc. or a non-volatile memory, such as a read only memory (ROM), a programmable ROM (PROM), an electrically programmable ROM (EPROM), an electrically erasable and programmable ROM (EEPROM), a flash memory device, a phase-change RAM (PRAM), a magnetic RAM (MRAM), a resistive RAM (RRAM), a Ferroelectric RAM (FRAM), etc. Also, the memory unit 190 may also be provided as a storage medium, such as a floppy disk, a hard disk or an optically readable medium, such as a CD ROM, DVD, etc.

The communication unit 180 may transmit the biometric record data provided as the single data packet structure through integration to a user's personal terminal, such as a smart phone, or an external device 300 (see FIG. 11), such as a hospital server. The communication unit 180 may include a wireless communication device, such as an LF transceiver, an RF transceiver or a Bluetooth device and set a wireless network with the external device 300 to transmit and receive data.

The state control unit 181 may activate or inactivate the wireless communication function of the communication unit 180 in a preset period, for example. The processor 150 may broadcast an advertising message in a state in which the wireless communication is activated by the state control unit 181. The external device 300 may transmit an advertising message reception signal to the watch module 100 in response to the advertising message. The processor 150 of the watch module 100 sets a wireless network in response to the advertising message reception signal to transmit biometric record data to the external device 300 in units of the single data packet.

When the wireless communication function is inactivated or when the wireless communication function has been activated but the advertising message reception signal corresponding to the advertising message is not transmitted from the external device, the processor 150 may store biometric record data in the memory unit 190 and then transmit the stored biometric record data obtained by integrating the ID of the watch module, the ID of the vital signal sensor, the biometric data and measurement time information on the biometric data when the wireless network is set.

Figure 5:
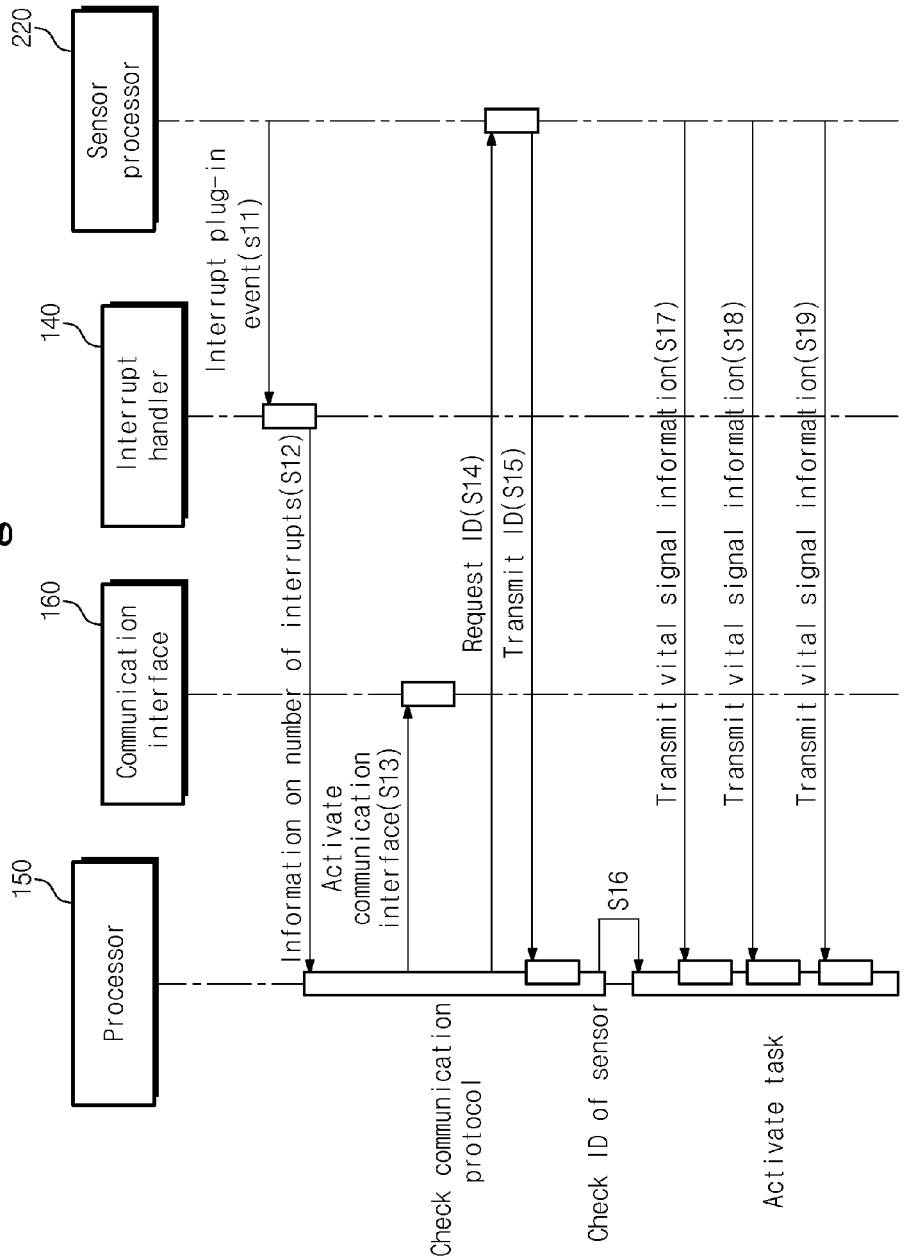
FIG. 5 is a flowchart of a method for measuring a vital signal according to an embodiment of the present disclosure.

FIG. 5 is a flowchart of a method for measuring a vital signal according to an embodiment of the present disclosure. Referring to FIGS. 1 to 5, the vital signal sensor 200 is connected to the watch module 100 and at the same time, the vital signal sensor 200 senses a change in power to recognize a connection of the vital signal sensor 200 and the watch module 100, and thus in step S11, the vital signal sensor 200 generates an interrupt plug-in event through a hardware signal to transmit the interrupt plug-in event to the watch module 100. The interrupt plug-in event generates interrupts a certain number of times representing communication protocol that the vital signal sensor 200 may support.

In step S12, the interrupt handle 140 of the watch module 100 counts the number of interrupts generated for a certain time, from the interrupt plug-in event transmitted from the vital signal sensor 200, and inputs information on the number of interrupts to the processor 150 of the watch module 100. In step S13, the processor 150 automatically recognizes a communication protocol supported by the vital signal sensor 200, according to the information on the number of interrupts input from the interrupt handler 140, and dynamically activates the communication interface 160 to correspond to the recognized communication protocol.

Thus, the watch module 100 and the vital signal sensor 200 may perform communication with each other according to an activated communication protocol, such as UART, USB, SPI, I²C, PIO, or ADC.

In order to check the function of the vital signal sensor 200, the processor 150 uses the activated communication interface 160 to transmit an ID request message for requesting the ID of the vital signal sensor 200 to the vital signal sensor 200. In step S15, the sensor processor 220 of the vital signal sensor 200 transmits the ID of the vital signal sensor 200 to the processor 150 of the watch module 100 in response to the ID request message.

In step S16, the processor 150 of the watch module 100 checks the function (e.g., the function of measuring blood sugar, blood pressure, a pulse wave, oxygen saturation, etc.) of the vital signal sensor 200 through the ID of the vital signal sensor 200 and activates a task to perform a job corresponding to the function of a corresponding vital signal sensor 200. If it is impossible to check the function of the vital signal sensor 200 through the requested ID, the watch module 100 may display a message representing a device recognition error.

Figure 6:
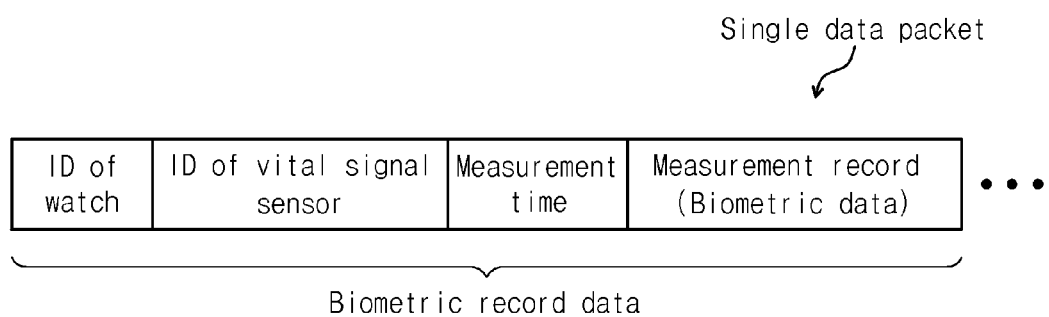
FIG. 6 is a diagram showing a data packet that a watch module configuring a vital signal measuring watch according to an embodiment of the present disclosure stores.

Subsequently, in steps S17 to S19, biometric data measured by the vital signal sensor 200 is transmitted to the watch module 100 according to the activated communication protocol. As shown in FIG. 6, the ID of the watch module (watch's ID), the ID of the vital signal sensor (vital signal sensor's ID), the biometric data collected from the vital signal sensor 200, and information on a measurement time when the biometric data has been collected may be integrated to be a single data packet, which may be stored in the memory unit 190. The watch's ID is a unique ID assigned to the watch module 100 and represents a user ID that identifies each of users.

As such, by integrating the user ID, the vital signal sensor's ID, the biometric data, and measurement time information to be in a single data packet format to form a material, it is possible to make meaningful data that contains user's personal information and biometric records. The integrated data may be transmitted to a personal mobile terminal, such as a smart phone, or an external device, such as a server for a medical service and thus enhance the efficiency of data usage.

Figure 7:
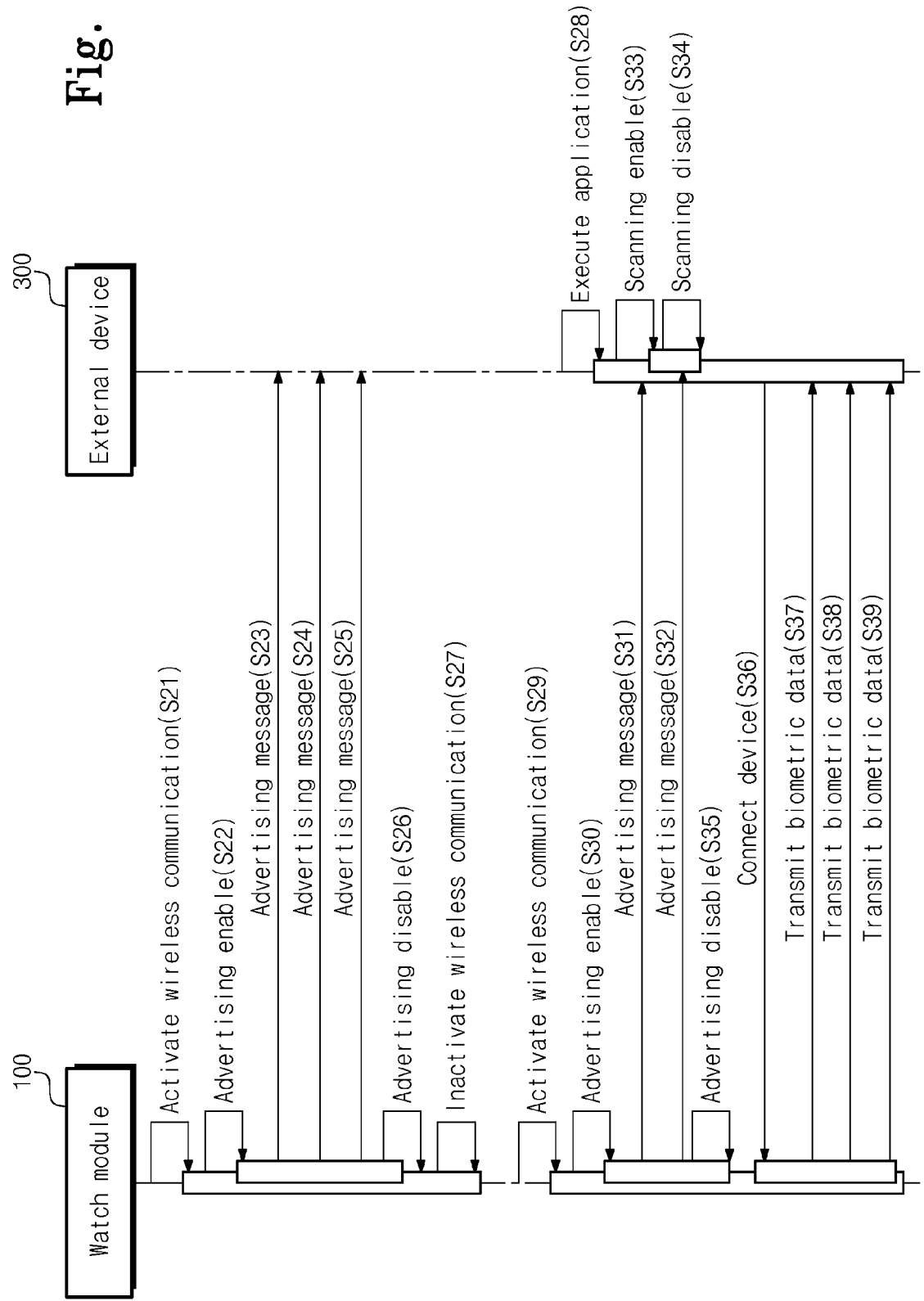
FIG. 7 is a flowchart of the process of transmitting data, from a watch module configuring a vital signal measuring watch according to an embodiment of the present disclosure, to an external device.

FIG. 7 is a flowchart of the process of transmitting data, from a watch module configuring a vital signal measuring watch according to an embodiment of the present disclosure, to an external device. The watch module 100 activates or inactivates a wireless communication function in a preset period in steps S21, S27, and S29. When the wireless communication function is activated, the watch module 100 operates an advertising function to transmit (broadcast) an advertising message to the external device 300 and then ends the operation of the advertising function in steps S22 to S26, S30 to S32, and S35.

When a corresponding application is executed by a user at the external device 300, such as a mobile terminal, e.g., a smart phone, an ambient signal is sensed through a user's mobile terminal, the advertising message is scanned and an operation ends in steps S28, S33, and S34. Next, in step S36, the external device 300 senses a signal sent from the watch module 100 and checks a user through the ID of the signal, and a device connection step at which an advertising message reception signal is transmitted from the external device 300 to the watch module 100 is performed, in which process a wireless network is set between the watch module 100 and the external device 300.

The watch module 100 transmits data accumulated until now to the external device 300 when the wireless network is set between the watch module 100 and the external device 300. That is, when wireless communication is not been set between the watch module 100 and the external device 300, such as when a wireless communication function is inactivated or when the wireless communication function has been activated but the advertising message reception signal corresponding to the advertising message is not transmitted from the external device 300, the processor 150 of the watch module 100 may utilize a 'delay tolerant' concept to store biometric record data in the memory unit 190 and then transmit stored biometric data to the external device 300 when the wireless network is set between the watch module and the external device 300. Thus, a user or medical team may check user's biometric data through the external device 300.

The user may obtain biometric data, such as blood sugar only with an action of connecting the vital signal sensor 200 easy to carry to the watch module 100, and since the biometric data is integrated with user ID, vital signal sensor's ID, and measurement time information to be single meaningful data and then transmitted to the external device 300 so that the data is transmitted to the user or his or her doctor through wireless communication, it is easy to collect measurement data for medical treatment. In addition, a medical service provider may utilize the transmitted biometric record data to provide appropriate prescription with a patient.

Figure 8:
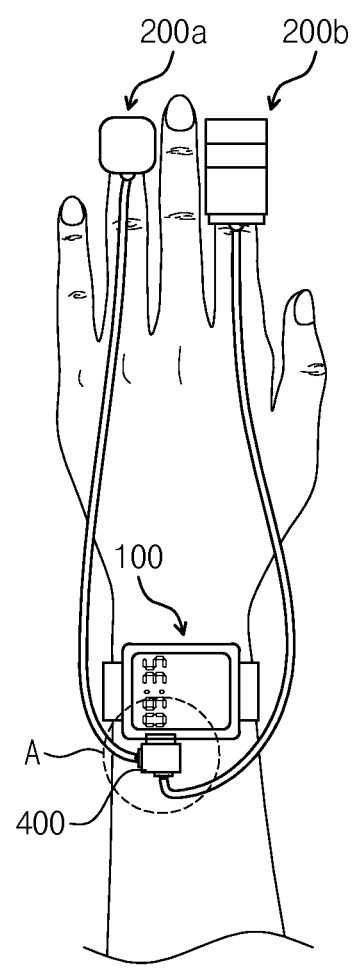
FIG. 8 is a diagram showing the usage state of a vital signal measuring watch according to another embodiment of the present disclosure.
Figure 9:
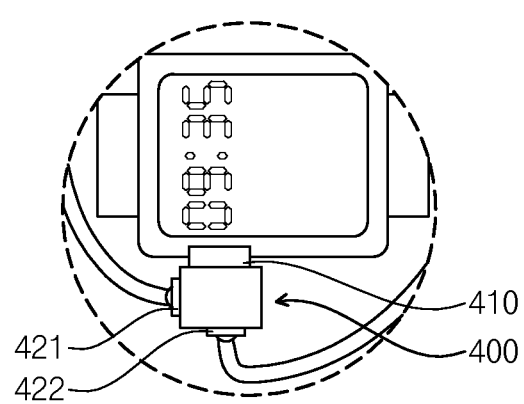
FIG. 9 is an enlarged view of the circled portion 'A' of FIG. 8.

FIG. 8 is a diagram showing the usage state of a vital signal measuring watch according to another embodiment of the present disclosure. FIG. 9 is an enlarged view of the circled portion 'A' of FIG. 8. Referring to FIGS. 8 and 9, it is possible to use a plurality of vital signal sensors 200a and 200b by connecting an extension port 400 to the communication port 130 of the watch module 100. The extension port 400 may include a connection port 410 engaged with the device receiving portion 111 to be connected to the communication port 130, and a plurality of device connection ports 421 and 421 connected to the plurality of vital signal sensors 200a and 200b measuring different vital signals.

Figure 10:
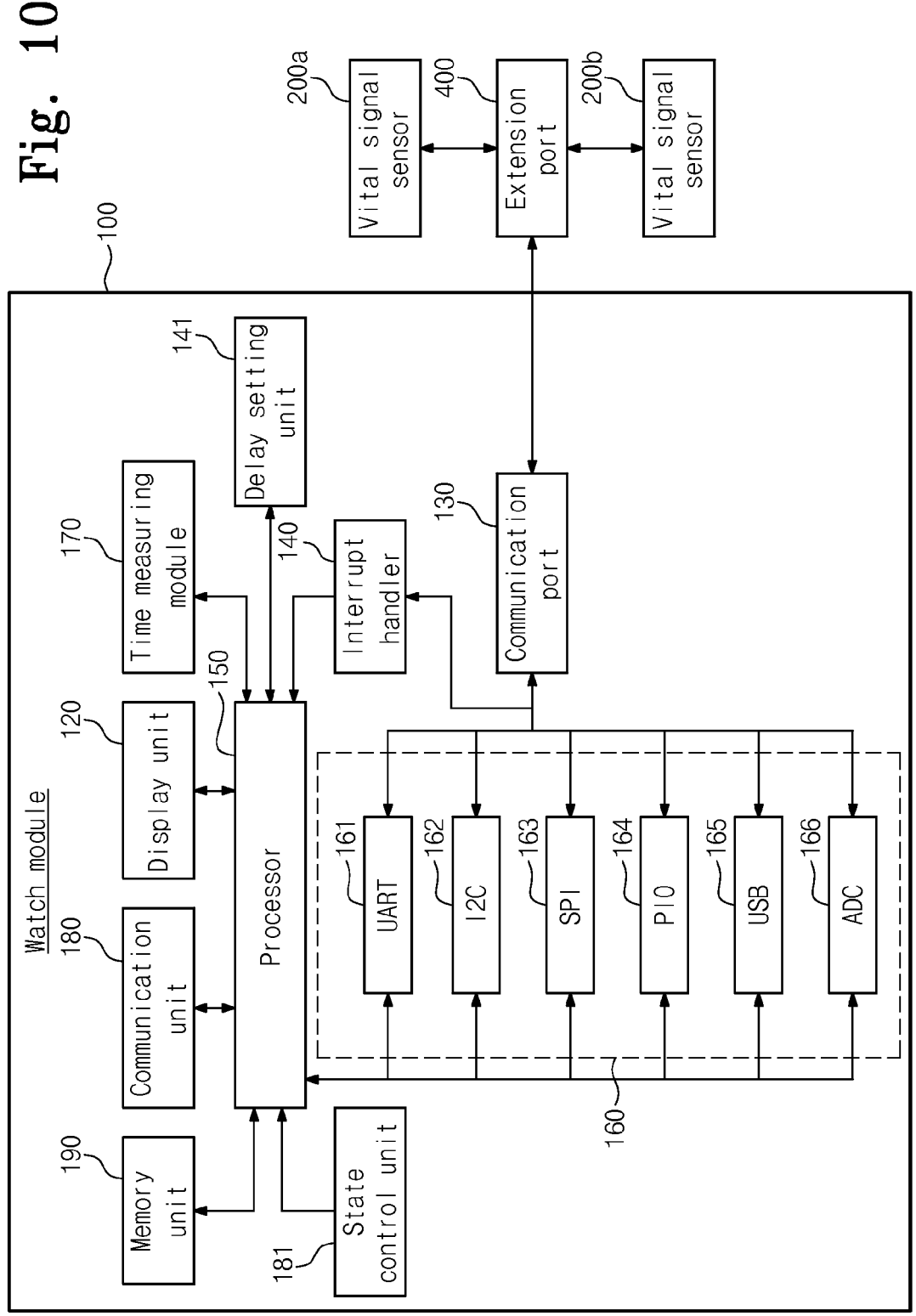
FIG. 10 is a block diagram of a vital signal measuring watch according to another embodiment of the present disclosure.

FIG. 10 is a block diagram of a vital signal measuring watch according to another embodiment of the present disclosure. In describing embodiments shown in FIGS. 8 to 10, the repetitive descriptions of the same components as those shown in FIGS. 1 to 3 are omitted. The same reference numeral is used for the same component in the accompanying drawings, if possible. Referring to FIGS. 8 to 10, the processor 150 recognizes one or more communication protocols corresponding to the vital signal sensors 200a and 200b, respectively. The communication interface 160 receives biometric data from each of the vital signal sensors 200a and 200b according to a communication protocol corresponding to each of the vital signal sensors 200a and 200b.

In order to prevent the collision of a plurality of interrupt plug-in events from the plurality of vital signal sensors 200a and 200b, a delay setting unit 141 sets a delay to be capable of sequentially processing the plurality of interrupt plug-in events from the plurality of vital signal sensors 200a and 200b. In order to prevent the collision between a plurality of pieces of biometric data from the plurality of vital signal sensors 200a and 200b, the delay setting unit 141 sets a delay to be capable of sequentially receiving the plurality of pieces of biometric data from the plurality of vital signal sensors 200a and 200b to transmit or store the received data to the external device 300 or in the memory unit 190.

Figure 11:
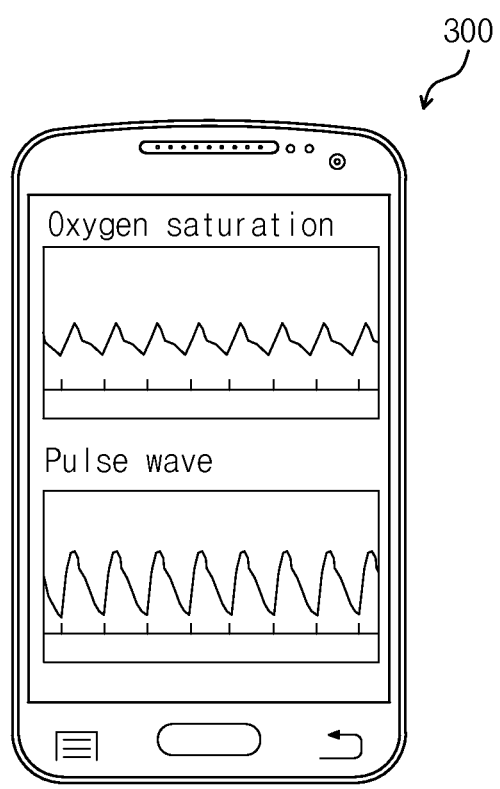
FIG. 11 is a diagram showing how an external device receives biometric record data from a vital signal measuring watch according to an embodiment shown in FIG. 8 and displays the received data.

FIG. 11 is a diagram showing how to receive and display biometric record data from a vital signal measuring watch according to an embodiment shown in FIG. 8. As could be seen in FIG. 11, data accumulated through the vital signal measuring unit 10 may be transmitted to the external device 300, such as a personal smart phone, and a user or medical team may check user's biometric data through a display screen. FIG. 11 represents that the external device 300 displays oxygen saturation and a pulse wave, but other vital signals may also be displayed.

Figure 12:
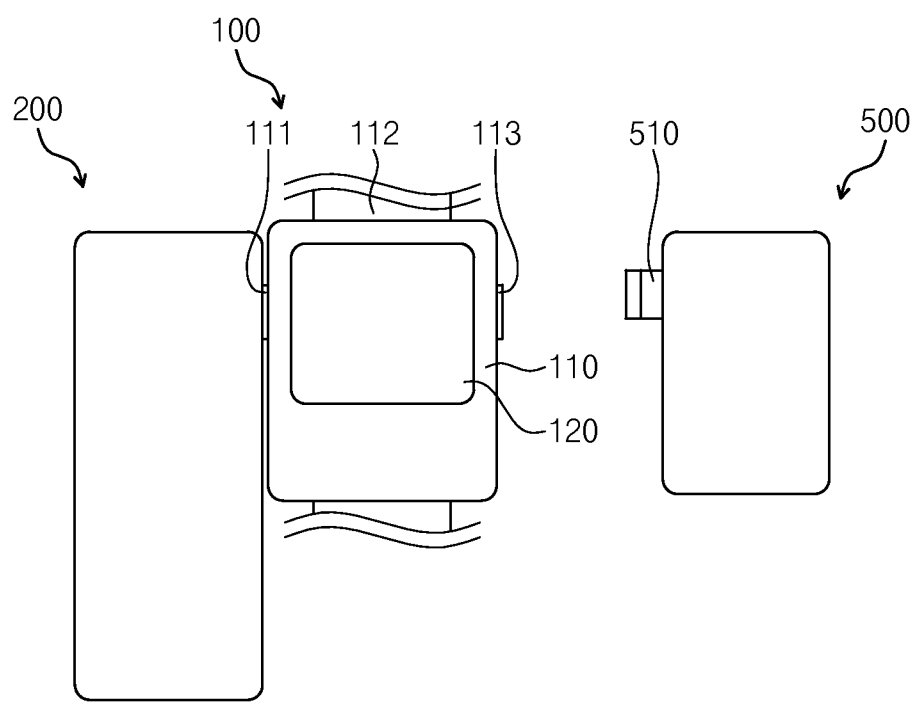
FIG. 12 is a diagram showing a watch module that configures a vital signal measuring watch according to an embodiment of the present disclosure, and a communication module.

FIG. 12 is a diagram showing a watch module that configures a vital signal measuring watch according to an embodiment of the present disclosure, and a communication module. In addition to installing the vital signal sensor 200 in the watch module 100 through the device receiving portion 111, the communication connector 510 of the communication module 500 may be additionally installed at the communication module connection port 113 of the watch module 100 to support other wireless communication in addition to the wireless communication provided for the vital signal measuring watch by default.

The watch module 100 may use wireless communication, such as Bluetooth Low Energy, IEEE 802.15.4 MAC, etc. to transmit biometric information to a user terminal, such as a smart phone, or the external device 300, such as a monitoring device in a hospital server, by using a real-time streaming technique so it is possible to monitor user's biometric information in real time. By identifying various vital signals collected from a user through the external device 300, it is possible to check the vital signal through a stream technique over time. Since depending on the case, it is possible to observe only required data in a specific vital signal or observe data measured for a specific time, the usage of data increases.

Since an embodiment according to the present disclosure enables all operations for vital signal measurement and data transmission to be performed only with an action of connecting the vital signal sensor 200 to the watch module in consideration of a users' age bracket and an action of executing an application in a smart phone, it provides an advantage that enables a user to easily and simply perform biometrics. Also, an embodiment according to the present disclosure enables the multiple devices of various vital signal sensors (a blood sugar meter, a sphygmomanometer, an oxygen saturation meter, a pulsimeter, etc.) to be linked to the watch module 100 provided with the shape of a wrist watch for a user who requires personal healthcare or has to measure medical data, to provide convenience when vital signals are measured.

As such, according to an embodiment of the present disclosure, since it is easy to use for measuring vital signals by an easy connection between the watch module 100 and the vital signal sensor 200 and by minimizing an operation for a communication function between the watch module 100 and the outside, a user who is unfamiliar with the usage of an electronic device may also easily use; since by utilizing the wireless transmission and reception function of the watch module 100, vital signals are transmitted to a personal mobile terminal (smart phone) or the outside, such as a hospital, each of users easily collects data; and since the usage of data increases, it may be helpful in providing an effective medical service.

Since the above embodiments are presented to help the understanding of the present disclosure, it should be understood that they do not limit the scope of the present disclosure and various variations thereto also belong to the scope of the present disclosure. The technical protective scope of the present disclosure should be defined by the technical spirit of the following claims and it should be understood that the technical protective scope of the present disclosure is not limited to the wording of the claims but actually reaches inventions having equivalent technical values.

The invention claimed is:

1. A vital signal measuring watch comprising:
   a watch module having a shape of a wrist watch, the watch module comprising a device receiving portion at one side of the watch module and a communication port in the device receiving portion; and
   a vital signal sensor connected to or disconnected from the device receiving portion, the vital signal sensor being connected to the communication port when the vital signal sensor is connected to the device receiving portion, and configured to transmit biometric data obtained by measuring vital signals to the communication port,
   wherein the vital signal sensor is configured to generate an interrupt plug-in event to transmit the event to the watch module when the vital signal sensor is connected to the communication port, and
   the watch module is configured to count a number of interrupts of the transmitted interrupt plug-in event, automatically recognize a communication protocol supported by the vital signal sensor according to the number of interrupts, and dynamically activate a communication interface to correspond to the recognized communication protocol to receive the biometric data from the vital signal sensor.

2. The vital signal measuring watch of claim 1, wherein the vital signal sensor is configured to sense a change in power when the vital signal sensor is connected to the communication port, to generate the interrupt plug-in event.

3. The vital signal measuring watch of claim 1, wherein the communication interface is provided to support different communication protocols, and
   a processor of the watch module is configured to activate at least one of the different communication protocols to correspond to the communication protocol supported by the vital signal sensor to dynamically activate the communication interface.

4. The vital signal measuring watch of claim 3, wherein the communication protocol comprises at least one of universal asynchronous receiver/transmitter (UART), universal serial bus (USB), serial peripheral interface (SPI), inter-integrated circuit bus (I²C), programmed input/output (PIO), and analog-to-digital converter (ADC).

5. The vital signal measuring watch of claim 1, wherein the watch module comprises:
   a housing having the device receiving portion at one side thereof;
   the communication port installed in the device receiving portion;
   an interrupt handler installed in the housing and configured to count the number of counts of the interrupt plug-in event;
   a processor installed in the housing and configured to automatically recognize the communication protocol supported by the vital signal sensor according to the number of interrupts;
   the communication interface installed in the housing, the communication interface being configured to be dynamically activated to correspond to the communication protocol by the processor, and configured to perform communication with the vital signal sensor according to the communication protocol to receive the biometric data from the vital signal sensor;
   a time measuring module installed in the housing, the time measuring module being configured to measure time information; and
   a display unit installed at an external side of the housing, the display unit being configured to display at least one of the time information and the biometric data.

6. The vital signal measuring watch of claim 5, wherein the watch module further comprises a memory unit, and
   the processor is configured to integrate biometric record data to be a single data packet to store the single data packet in the memory unit, the biometric record data comprising an ID of the watch module, an ID of the vital signal sensor, the biometric data and measurement time information on the biometric data.

7. The vital signal measuring watch of claim 6, wherein the watch module further comprising a communication unit that is configured to transmit, to an external device, the biometric record data provided as the single data packet through integration.

8. The vital signal measuring watch of claim 7, wherein the watch module further comprises a state control unit configured to activate or inactivate a wireless communication function of the communication unit in a preset period, and
   the processor is configured to broadcast an advertising message in a state in which the wireless communication function is activated, and set a wireless network in response to an advertising message reception signal from the external device corresponding to the advertising message.

9. The vital signal measuring watch of claim 5, wherein the watch module further comprises a communication module connection port at the housing, and a communication module connected to the communication module connection port to support wireless communication with an external device.

10. The vital signal measuring watch of claim 5, wherein the watch module further comprises a connection port installed at the device receiving portion to be connected to the communication port, and an extension port comprising a plurality of device connection ports connected to a plurality of vital signal sensors that measures different vital signals.

11. The vital signal measuring watch of claim 10, wherein the processor is configured to recognize one or more communication protocols corresponding to each of vital signal sensors, and
the communication interface is configured to receive the biometric data from each of the vital signal sensors according to the communication protocol corresponding to each of the vital signal sensors.

12. The vital signal measuring watch of claim 10, wherein the watch module further comprises a delay setting unit configured to set a delay to prevent collision of a plurality of interrupt plug-in events from the plurality of vital signal sensors to sequentially process the plurality of interrupt plug-in events.

13. The vital signal measuring watch of claim 5, wherein the processor is configured to transmit an ID request message for checking a function of the vital signal sensor to the vital signal sensor by using the activated communication interface and activate a task corresponding to an ID of the vital signal sensor received from the vital signal sensor in response to the ID request message.

14. The vital signal measuring watch of claim 1, wherein the vital signal comprises at least one selected from blood sugar information, blood pressure information, oxygen saturation information, and pulse wave information.

15. A vital signal measuring watch comprising:
a watch module having a shape of a wrist watch and a device receiving portion at one side thereof,
wherein the watch module is configured to count a number of interrupts of the interrupt plug-in event transmitted from a vital signal sensor when the vital signal sensor is connected to the device receiving portion, automatically recognize a communication protocol supported by the vital signal sensor according to the number of interrupts, and dynamically activate a communication interface to correspond to the recognized communication protocol to receive biometric data from the vital signal sensor.

16. A method for measuring a vital signal, the method comprising:
counting, by a watch module, a number of interrupts of an interrupt plug-in event transmitted from a vital signal sensor when the vital signal sensor is connected to the watch module, automatically recognizing a communication protocol supported by the vital signal sensor according to the number of interrupts, and dynamically activating a communication interface to correspond to the communication protocol; and
receiving, by the watch module, biometric data from the vital signal sensor by using the activated communication interface.

17. The method of claim 16, further comprising:
integrating and storing, by the watch module, biometric record data to be a single data packet, the biometric record data comprising an ID of the watch module, an ID of the vital signal sensor, the biometric data and measurement time information on the biometric data; and
transmitting, by the watch module, the biometric record data provided as the single data packet through integration, to an external device.

18. The method of claim 17, wherein the transmitting of the biometric record data to the external device comprises:
activating or inactivating, by the watch module, a wireless communication function in a preset period;
broadcasting, by the watch module, an advertising message in a state in which the wireless communication function is activated; and
setting, by the watch module, a wireless network in response to an advertising message reception signal from the external device corresponding to the advertising message.

19. The method claim 16, wherein the activating of the communication interface comprises setting a delay to sequentially process the plurality of interrupt plug-in events to prevent collision of a plurality of interrupt plug-in events from a plurality of vital signal sensors.

20. The method of claim 16, further comprising, between the activating of the communication interface and the receiving of the biometric data:
transmitting, by the watch module, an ID request message for checking a function of the vital signal sensor to the vital signal sensor by using the activated communication interface; and
activating, by the watch module, a task corresponding to an ID of the vital signal sensor received from the vital signal sensor in response to the ID request message.

* * * * *